(12) United States Patent
Ofori

(10) Patent No.: US 6,191,060 B1
(45) Date of Patent: *Feb. 20, 2001

(54) RECLAMATION OF METAL CATALYSTS USED IN THE PRODUCTION OF DIARYL CARBONATES

(75) Inventor: John Yaw Ofori, Niskayuna, NY (US)

(73) Assignee: General Electric Company, Schenectady, NY (US)

(*) Notice: Under 35 U.S.C. 154(b), the term of this patent shall be extended for 0 days.

This patent is subject to a terminal disclaimer.

(21) Appl. No.: 09/215,362

(22) Filed: Dec. 18, 1998

(51) Int. Cl.[7] ............... B01J 20/34; C02F 1/72
(52) U.S. Cl. ............... 502/28; 502/22; 502/27; 210/681; 210/688
(58) Field of Search ............... 502/20, 25, 22, 502/27, 28; 210/681, 688

(56) References Cited

U.S. PATENT DOCUMENTS

| | | |
|---|---|---|
| 4,187,242 | 2/1980 | Chalk . |
| 5,101,052 | 3/1992 | Meyer et al. . |
| 5,231,210 | 7/1993 | Joyce et al. . |
| 5,284,964 | 2/1994 | Pressman et al. . |
| 5,399,734 | 3/1995 | King, Jr. et al. . |
| 5,498,789 | 3/1996 | Takagi et al. . |
| 5,648,510 * | 7/1997 | Harada et al. ............ 558/274 |
| 5,760,272 | 6/1998 | Pressman et al. . |
| 5,821,377 * | 10/1998 | Buysch et al. ............ 558/274 |
| 5,892,091 * | 4/1999 | Harada et al. ............ 558/270 |
| 5,908,952 * | 6/1999 | Pressman et al. ............ 558/274 |
| 5,981,788 * | 11/1999 | Ofori et al. ............ 558/274 |
| 6,001,768 * | 12/1999 | Buysch et al. ............ 502/230 |

FOREIGN PATENT DOCUMENTS

| | | |
|---|---|---|
| 0 801 052 | 4/1996 | (DE) . |
| 0 507 546 | 10/1992 | (EP) . |
| 0 521 480 | 1/1993 | (EP) . |

* cited by examiner

*Primary Examiner*—Steven P. Griffin
*Assistant Examiner*—Christina Ildebrando

(57) ABSTRACT

A method for efficient reclamation of metal catalyst species from aqueous extract streams diaryl cabonate synthesis, comprising treating a metal-containing aqueous extract stream of a mixture from the production of diaryl carbonates with a precipitating agent effective to selective precipitate one or more metal catalyst species from the extract. Use of these methods substantially reduces both financial and environmental concerns for the preparation of diaryl carbonates.

12 Claims, No Drawings

RECLAMATION OF METAL CATALYSTS USED IN THE PRODUCTION OF DIARYL CARBONATES

BACKGROUND OF THE INVENTION

The present invention relates to methods for reclaiming metal catalyst species. In particular, this invention relates to methods for isolating and recycling palladium and cobalt catalysts used in the production of diaryl carbonates.

Diaryl carbonates, and diphenyl carbonate in particular, are valuable monomer precursors for the preparation of polycarbonates by melt transesterification. An advantageous route for the synthesis of diaryl carbonates is the direct carbonylation of aromatic hydroxy compounds by carbon monoxide and an oxidant in the presence of a catalyst.

A wide range of catalysts may be used in this preparation of diaryl carbonates. For example, U.S. Pat. No. 4,187,242 to Chalk discloses catalysts derived from Group VIIIB metals, i.e., metals selected from the group consisting of ruthenium, rhodium, palladium, osmium, iridium and platinum, or complexes thereof. U.S. Pat. Nos. 5,231,210 to Joyce, et al., U.S. Pat. Nos. 5,284,964 and 5,760,272 to Pressman et al., and 5,399,734 to King, Jr., et al. further disclose the use of co-catalysts, including metal co-catalyst species such as cobalt pentadentate complexes and complexes of cobalt with pyridines, bipyridines, terpyridines, quinolines, isoquinolines, aliphatic polyamines such as ethylenediamine, crown ethers, aromatic or aliphatic amine ethers such as cryptanes, and Schiff bases, in combination with organic co-catalysts such as terpyridines and quaternary ammonium or phosphonium halides. In U.S. Pat. No. 5,498,789 to Takagi et al., the catalyst system consists of a palladium compound, at least one lead compound, at least one halide selected from quaternary ammonium halides and quaternary phosphonium halides, and optionally at least one copper compound.

As can be seen from the above brief review, the crude reaction mixtures arising from the production of diaryl carbonates can contain complex mixtures of catalyst and co-catalyst metals, and organic products and by-products. The cost of commercially implementing direct oxidative carbonylation is heavily dependent on a combination of the efficiency of the catalyst package and on the ability to reclaim the expensive catalyst components and unconverted aromatic starting material. While palladium represents the primary material expense, it is also important to control the usage of other, less expensive materials, such as cobalt, manganese, or lead both from the cost and environmental points of view. Accordingly, there remains a need in the art for efficient, convenient methods for the reclamation of the metal catalysts and cocatalysts used in the carbonylation of aromatic hydroxy compounds to produce diary carbonates.

SUMMARY OF THE INVENTION

The above-discussed and other drawbacks and deficiencies of the related art are alleviated by the method of the present invention for reclaiming metal catalyst species from aqueous extract streams arising from the crude reaction mixtures produced by oxidative carbonylation of aromatic hydroxy compounds, comprising treating metal-containing aqueous extract streams with a precipitating agent effective to selectively precipitate at least one metal separately or as a mixture from the treated extract. Such reclamation substantially reduces both economic and environmental concerns in the preparation of diaryl carbonates.

DETAILED DESCRIPTION OF THE INVENTION

The present method makes possible efficient reclamation of metal catalyst and/or co-catalyst species (referred to hereinafter collectively as "metal catalysts"), particularly palladium and cobalt, from crude mixtures resulting from the production of diaryl carbonates. The method comprises treating metal-containing aqueous extract streams containing ruthenium, rhodium, palladium, osmium, iridium, platinum, iridium, manganese, lead, zinc, cobalt, copper, and mixtures thereof with a precipitating agent effective to selectively precipitate the metals separately or as a mixture from the treated extract. In a preferred embodiment, palladium and cobalt are precipitated together or separately.

The crude reaction mixture obtained when diaryl carbonates are made by direct oxidative carbonylation of aromatic hydroxy compounds contains the excess starting aromatic hydroxy compounds, the product diaryl carbonate, and organic and inorganic by-products. The catalyst metals in this crude reaction mixture, e.g., ruthenium, rhodium, palladium, osmium, iridium, platinum, iridium, manganese, lead, zinc, copper, cobalt, and mixtures thereof, may be removed by solvent extraction using an aqueous acid, aqueous salt, or aqueous acid/salt mixture.

Generally, species effective to extract the catalyst metals include strong electrolytes with high water solubility (to enable phase separation with the organic phase), low hydroxyaryl and diaryl carbonate solubility, and strong complexing affinities with the metals to be extracted, particularly palladium. Acids are most useful for palladium extraction.

Preferred acids include, but are not limited to, inorganic acids such as hydrochloric acid and hydrobromic acid. Salts effective in metal extraction include, but are not limited to, alkali metal and alkaline earth salts of halides. Preferred salts are sodium, potassium, calcium, and magnesium salts of chlorine and bromine, particularly sodium chloride and sodium bromide. Combinations of the foregoing acids and salts may also be used.

The concentration of acid or acid/salt mixture effective to extract the metal catalysts from the crude reaction mixture is readily empirically determined by one of ordinary skill in the art. In general, an effective concentration is in the range from about 1 percent by weight to about 18 percent by weight, and preferably in the range from about 3 percent by weight to about 10 percent by weight.

Reclamation of metals from the extract is achieved by the addition of a precipitating agent which forms an effectively water-insoluble compound with the catalyst metals. Effective precipitating agents have at least partial water solubility in the absence of the catalyst metals, and produce at least partially water-insoluble compounds in combination with he metals. Effective precipitation with certain agents may require adjustment of the pH of the aqueous extract stream. Determination of which precipitating agents require adjustment of the pH of the extract stream is easily ascertained by one of ordinary skill in the art.

Suitable precipitating agents effective in precipitation of at least one metal catalyst from the aqueous extract include, but are not limited to, acetylacetone and alkali metal salts of acetylacetonates such as sodium acetylacetonate monohydrate; and oxalic acid and alkali metal salts of oxalates such as sodium oxalate. Salts are generally preferred.

The concentration of precipitating agent in the aqueous extract effective to result in precipitation of metal catalysts may be empirically determined by one of ordinary skill in the art. In general, an effective concentration in the aqueous extract is in the range from about 0.1 percent by weight to about 30 percent by weight, and preferably in the range from about 0.1% percent by weight to about 1% percent by weight. A concentrated aqueous solution of the precipitating agent may be prepared and used for the precipitation.

In a particularly advantageous embodiment, two or more metals are precipitated from the aqueous extract serially, by adding the precipitant in stages. Thus, where the metal-precipitant salts have differing solubilities, the addition of a first portion of the precipitant results predominantly in the precipitation of the less soluble metal precipitant salt. Addition of a second portion of the precipitating agent results in the precipitation of the more soluble metal-precipitant salt, and so on. A filtration or other solid-liquid separation process suffices to separate the first precipitate from the filtrate before the next precipitation is performed. As shown in Example 1 below, treatment of an aqueous mixture of palladium and cobalt with a limited quantity of sodium acetylacetonate, followed by isolation of the precipitate, results in essentially complete separation of the palladium and cobalt, with the precipitated solid containing virtually all of the palladium and a minimal amount of cobalt, and the filtrate containing virtually all of the cobalt and a minimal amount of palladium. Addition of a further quantity of sodium acetylacetonate to the filtrate results in substantially complete precipitation of cobalt from the filtrate.

In a particularly preferred feature of this embodiment, the serial separation process is robust, in the sense that the addition of the precipitating agent, even when in excess of that needed to precipitate only the first metal, does not lead to co-precipitation of all compounds unless a significantly large excess of the precipitant is added. Alternatively, two different precipitants are used to obtain selective, serial precipitation. Such serial separation is desirable where one or more metals may require subsequent unique treatment in order to render them reusable as a catalyst in the synthesis of diaryl carbonates.

In another embodiment, combined precipitation of at least two metals is achieved by omitting the filtration steps to separate the individual metal compounds before the addition of further precipitant. Such combined precipitation with sodium acetylacetonate results in removal at least 99.9% of palladium and about 98.6% of cobalt from an aqueous solution (Example 3).

The following examples are provided by way of example only, and should not be read to limit the scope of the invention.

EXAMPLE 1

A mixture of 0.703 g (3.96 mmol) $PdCl_2$, 0.797 g (6.18 mmol) of $CoCl_2$, and 1.217 g (20.8 mmol) of NaCl were dissolved in 14.5 g of water (total mass=17.217 grams). 7.5 g of this solution was then diluted with 22.9 g of water to yield a solution having a total mass of 30.4 g, and containing 0.3062 g (1.727 mmol) of $PdCl_2$, 0.3472 g (2.674 mmol) of $CoCl_2$, and 0.5301 g (9.062 mmol) of NaCl. An aqueous solution of sodium acetylacetonate monohydrate (Na(acac)) having 0.780 g (5.567 mmole) of Na(acac) dissolved in 4.5 g of water was added in stages to the foregoing aqueous $PdCl_2/COCl_2/NaCl$ solution. After the addition of the Na(acac) solution was complete, a yellowish-brown precipitate developed after 30 minutes of mixing. The solution was filtered to separate the precipitate from a pink filtrate. A quantity of water was used to wash the remaining solid out of the reaction vial, filtered, and combined with the first filtrate.

The filtrate was analyzed for the presence of metals by inductively coupled plasma spectroscopy (ICP). Analysis indicated the presence of less than 10 ppm (parts per million) (below the detection limit) of palladium and 2480 ppm of cobalt. The dried solid was also analyzed by dissolving the solid in a warm solution of HCl/NaCl, which was subsequently subjected to ICP spectroscopy. The spectroscopy indicated the presence of 31.61% by weight palladium (theoretical content of palladium as palladium (II) acetylacetonate is 34.9% by weight), and 0.385% by weight cobalt. These data indicate essentially complete separation of the palladium and cobalt, with the precipitated solid containing virtually all of the palladium and a minimal amount of cobalt, and the filtrate containing virtually all of the cobalt and a minimal amount of palladium.

EXAMPLE 2

A further 1.944 g (13.874 mmole) of Na(acac) dissolved in about 5 g of water was added to the filtrate of Example 1, resulting in the precipitation of a pink solid. The solid was filtered, dried, and analyzed. The analysis indicated the presence of 15.69% by weight of cobalt (theoretical amount of the cobalt content as cobalt (III) acetylacetonate is 16.53%). Analysis of the filtrate indicated the presence of 84.1 ppm of cobalt, and less than 10 parts ppm of palladium (below the detection limit). These results indicate substantially complete precipitation of cobalt from the filtrate obtained from the palladium precipitation step.

EXAMPLE 3

A mixture of 0.766 g (4.32 mmol) of $PdCl_2$, 0.722 g (5.56 mmol) of $CoCl_2$, and 0.733 g (12.53 mmol) of NaCl were dissolved in 14.5 g (833.33 mmol) of water. An aqueous solution of 2.7522 g (26.93 mmol; theoretical quantity needed to precipitate all of the Pd(II) and Co(III) present in the solution is 3.576 g, and theoretical quantity needed to precipitate all of the Pd(II) and Co(II) present in the solution is 2.768 g) of sodium acetylacetonate monohydrate dissolved in 21.7 g of water was added in stages to the foregoing aqueous $PdCl_2/CoCl_2/NaCl$ solution. A precipitate developed, which was filtered, dried, and weighed. The total weight of the solid was 3.074 g. The theoretical amount of precipitate is 1.3159 g of Pd(II)(acac); 1.4299 g of Co(II)(acac); 1.9811 g of (Co)(III)(acac).

The filtrate was analyzed for the presence of metals by ICP spectroscopy, and was shown to contain 10 ppm palladium and 150 ppm cobalt. With no precipitation, expected palladium levels would be 11,030, ppm, and expected cobalt levels would be 10,891 ppm. It is thus estimated that greater than 99.9% of palladium and approximately 98.6% of the cobalt have been reclaimed from the filtrate.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for reclaiming metal catalyst species from a metal-containing aqueous extract stream from diaryl carbonate production mixtures, said method comprising treating a metal-containing aqueous extract stream of a mixture from the production of diaryl carbonate with a first portion of a precipitating agent effective to precipitate at least one first metal catalyst species from the extract stream.

2. The method of claim 1, wherein the metals in the aqueous extract stream are selected from the group consisting of ruthenium, rhodium, palladium, osmium, platinum, iridium, manganese, lead, zinc, cobalt, copper, and mixtures thereof.

3. The method of claim 1, wherein the precipitated metal catalyst species is palladium, cobalt, or a mixture thereof.

4. The method of claim 1, wherein the precipitating agent is selected from the group consisting of acetylacetone, oxalic acid, salts of acetylacetonates and salts of oxalates.

5. The method of claim 1, wherein the precipitating agent is sodium acetylacetonate which results in precipitation of palladium or cobalt salts of acetylacetonate or mixtures thereof from the extract stream.

6. The method of claim 1, comprising further treating the treated extract stream with a second portion of the same or a different precipitating agent effective to precipitate at least one second metal catalyst species from the treated extract stream.

7. The method of claim 6, further comprising separating the precipitated at least one first metal catalyst species from the extract stream prior to the addition of the second portion of precipitating agent.

8. The method of claim 6, wherein the metals in the aqueous extract stream are selected from the group consisting of ruthenium, rhodium, palladium, osmium, platinum, iridium, manganese, lead, zinc, cobalt, copper, and mixtures thereof.

9. The method of claim 8, wherein the at least one first precipitated metal catalyst species is palladium, and cobalt is also precipitated as at least one second metal catalyst species.

10. The method of claim 9, wherein the first portion of the precipitating agent is sodium acetylacetonate which results in precipitation of palladium salts of acetylacetonate from the treated extract stream, and the second portion of the precipitating agent is sodium acetylacetonate which results in precipitation of cobalt salts of acetylacetonate from the treated extract stream.

11. The method of claim 6, wherein each precipitating agent is selected from the group consisting of acetylacetone, oxalic acid, salts of acetylacetonates and salts of oxalates.

12. A method for reclaiming metal catalyst species from a metal-containing aqueous extract stream from diaryl carbonate production mixtures, said method comprising the steps of:

adding a first portion of sodium acetylacetonate to a metal-containing aqueous extract stream of a mixture from the production of diaryl carbonate to precipitate at least one first metal catalyst species from the extract stream;

separating the at least one first metal catalyst species from the extract stream; and adding a second portion of sodium acetylacetonate to the extract stream to precipitate at least one second metal catalyst species from the extract stream.

* * * * *

UNITED STATES PATENT AND TRADEMARK OFFICE
CERTIFICATE OF CORRECTION

PATENT NO.    : 6,191,060 B1
DATED         : February 20, 2001
INVENTOR(S)   : John Yaw Ofori It is certified that error appears in the above-identified patent and that said Letters Patent is hereby corrected as shown below:

Title page,
Item [57], ABSTRACT,
Line 2, the word "cabonate" should read -- carbonate --.
Line 2, the phrase "streams diaryl" should read -- streams of diaryl --.
Line 5, the word "selective" should read -- selectively --.

Column 1,
Line 50, the word "diary" should read -- diaryl --.

Column 2,
Line 49, the word "he" should read -- the --.

Column 3,
Line 49, the formula "CoCI$_2$" should read -- CoCl$_2$ --.
Line 58, the formula "COCI$_2$" should read -- CoCl$_2$ --.

Column 4,
Lines 19-20, the phrase "is 20 16.53%" should read -- is 16.53% --.

Signed and Sealed this

Twenty-fourth Day of September, 2002

*Attest:*

*Attesting Officer*

JAMES E. ROGAN
*Director of the United States Patent and Trademark Office*